United States Patent
Regnier et al.

(10) Patent No.: US 10,967,151 B2
(45) Date of Patent: Apr. 6, 2021

(54) STEERABLE CATHETER FOR THE IMPLANTATION OF A LEADLESS CARDIAC CAPSULE

(71) Applicant: CAIRDAC, Antony (FR)

(72) Inventors: Willy Regnier, Longjumeau (FR); Florian Leveque, Brétigny-sur-Orge (FR); Julien Dohin, Antony (FR); Jean-Baptiste Pourchet, Pompey (FR); Perrine Chaffotte, Malleloy (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 254 days.

(21) Appl. No.: 16/237,749

(22) Filed: Jan. 1, 2019

(65) Prior Publication Data
US 2020/0206465 A1   Jul. 2, 2020

(51) Int. Cl.
*A61M 25/01* (2006.01)
*A61M 25/06* (2006.01)
*A61N 1/05* (2006.01)
*A61M 25/00* (2006.01)

(52) U.S. Cl.
CPC .... *A61M 25/0147* (2013.01); *A61M 25/0662* (2013.01); *A61N 1/0587* (2013.01); *A61M 2025/0004* (2013.01); *A61M 2025/0175* (2013.01)

(58) Field of Classification Search
CPC .......... A61M 25/0147; A61M 25/0662; A61M 25/0053; A61M 2025/0004; A61M 2025/0175; A61N 1/0587
See application file for complete search history.

(56) References Cited

U.S. PATENT DOCUMENTS

| | | | |
|---|---|---|---|
| 2010/0217184 A1* | 8/2010 | Koblish | A61M 25/0141 604/95.01 |
| 2014/0249543 A1 | 9/2014 | Berthiaume et al. | |
| 2014/0378992 A1 | 12/2014 | Ollivier | |
| 2015/0051615 A1 | 2/2015 | Schmidt et al. | |
| 2016/0271388 A1* | 9/2016 | Ollivier | A61N 1/056 |
| 2016/0296730 A1* | 10/2016 | Zhou | A61F 2/2433 |
| 2017/0266410 A1* | 9/2017 | Farrell | A61M 25/0147 |
| 2018/0178007 A1* | 6/2018 | Shuros | A61N 1/0573 |

\* cited by examiner

*Primary Examiner* — Kathleen S Holwerda
*Assistant Examiner* — Brooke Labranche
(74) *Attorney, Agent, or Firm* — Steven M. Greenberg, Esq.; Shutts & Bowen LLP

(57) ABSTRACT

A steerable catheter comprises a mobile tube and an intermediate tube, coaxial with each other, which extend from a proximal end to a distal end of the catheter and are telescopically mounted into each other with possibility of mutual rotation and axial translation. The mobile tube comprises a central lumen extending from the proximal end to the distal end. The intermediate tube comprises, along its whole length, a longitudinal notch radially offset in a direction of offset with respect to the axis of the steerable catheter and extending axially from the proximal end to the distal end. The longitudinal notch contains a cable adapted to undergo a traction exerted from the proximal end, the traction generating a bending of the steerable catheter directed towards the offset direction. The steerable catheter further comprises around the intermediate tube a sealed external sheath surrounding the intermediate tube over its periphery and covering the longitudinal notch over its length.

11 Claims, 2 Drawing Sheets

STEERABLE CATHETER FOR THE IMPLANTATION OF A LEADLESS CARDIAC CAPSULE

BACKGROUND OF THE INVENTION

Field of the Invention

The invention relates to accessories (or "tools") for implanting (or "delivering") implantable medical devices, i.e. for positioning a device at a chosen implantation site in the organism of a patient.

The invention more particularly relates to the accessories for implanting a device of the autonomous implantable capsule type.

Such a device, hereinafter referred to as "autonomous capsule", "leadless capsule", or simply "capsule", is in the form of a capsule implanted in a cardiac chamber (ventricle, atrium or even arterial left chamber of the heart). The capsule is autonomous, i.e. it is devoid of any physical connection to an implanted main device (such as a stimulation pulse generator casing) or non-implanted main device (external peripheral device such as a programmer or a monitoring device for remote follow-up of the patient). For that reason, such type of device is said "leadless", to distinguish it from the electrodes or sensors arranged at the distal end of a conventional lead, along the whole length of which run one or several conductors galvanically connecting the electrode or the sensor to a generator connected to an opposite, proximal end of the lead.

In this case of a cardiac application, the leadless capsule continuously monitors the patient's rhythm and if necessary delivers to the heart stimulation, resynchronization and/or defibrillation electrical pulses in case of rhythm disorders detected by the capsule. The capsule may be an epicardic capsule, fastened to the external wall of the heart, or an endocavitary capsule, fastened to the internal wall of a ventricular or atrial chamber, or also a capsule fastened to the wall of a vessel near the myocardium.

The invention is however not limited to the implantation of a particular type of capsule, nor even of leadless implant. The autonomous character of the capsule is not in itself a necessary feature of the invention, which is as well applicable to many other types of implantable medical devices, whatever their functional destination is, cardiac or other, for example capsules intended to diffuse in situ an active pharmacological agent.

Description of the Related Art

US 2009/0171408 A1 (Solem), US 2017/0151429 A1 (Regnier) and WO 2018/122244 A1 (Regnier) describe various examples of such intracardiac leadless capsules.

The capsules comprise various electronic circuits, sensors, etc., as well as wireless communication transceiver means for the remote exchange of data, the whole being integrated in a body of very small size able to be implanted in sites of difficult access or leaving small room, such as the ventricle apex, the internal wall of the atrium, etc. For their fastening in situ at the implantation site, these capsules are provided at their distal end with an anchoring member adapted to penetrate the tissues of a body wall. A typical example of such an anchoring member comprises a protruding helical screw axially extending the capsule body and intended to enter the cardiac tissue by being screwed thereinto at the implantation site. There exist other types of anchoring members, with, for example, pins, hooks, fins, etc., penetrating the tissues to permanently fasten the medical device thereto.

The implantation of endocavitary leadless capsules (i.e. capsules to be fastened to the inner wall of a ventricular or atrial chamber, as opposed to epicardic capsules, fastened to the outer wall of the heart) entails significant implantation constraints, in particular due to the approach way that requires passing through the peripheral venous network.

Indeed, due to the relatively large dimensions of present leadless capsules, which have a typical diameter of about 4 to 7 mm for a length of 15 to 40 mm, with an object of such a size there exists no upper-way procedure, i.e. via the subclavian vein, to accede to a cardiac chamber, in particular to reach the bottom of the right ventricle. It is hence necessary to use a different access, starting from a femoral access site, then going along the inferior vena cava up to the heart.

Such a femoral access is more tricky, in particular due to the significant angulation between the inferior vena cava and the axis of the right ventricle. In the case of an upper-way access, when arriving into the atrium, the distal portion of the implantation catheter is naturally directed towards the right ventricle apex, and it is only needed to push on the catheter to pass through the tricuspid valve and to reach the bottom of the ventricle, into which the anchoring member will be screwed after having docked to the wall. On the other hand, in the case of a femoral access, once the atrium is reached, it is necessary to operate a tilting of the distal end of the catheter to direct this end towards the ventricle and to allow it to pass through the tricuspid valve and to continue its progression in the good direction, towards the bottom of the ventricle.

There exists for that purpose steerable catheters, which are well-known implantation tools whose distal end is operable from a handle located at the opposite end, on the proximal side, so that such a steering operation can be performed, under an image intensifier, in the atrium.

Such a steerable catheter and the way to proceed with the implantation are described in particular in US 2014/0378991 (Ollivier). The implantation tool disclosed by this document further comprises a cylindrical protective tip extending the steerable catheter at its distal portion and containing the capsule to be implanted. This capsule is coupled to a sub-catheter (or "delivery catheter") inserted into the central inner lumen of the main catheter (or "guide catheter"), and is maintained in retracted position in the tip during the whole duration of the approaching operation. The capsule and the delivery catheter are temporarily connected through a simple disengageable mechanism allowing a complete screwing of the capsule into the cardiac wall, then the final release thereof. The telescopic configuration of the delivery catheter allows ejecting the capsule out of the protective tip and beyond the latter over several centimetres, making it possible in any circumstance to fully and accurately bring the capsule to the bottom of the ventricle.

The guide catheter is operated by the practitioner by means of a suitable handle comprising a mechanism comparable to that described in U.S. Pat. No. 5,891,088 (Thompson et al.) and U.S. Pat. No. 5,462,527 (Stevens-Wright et al.). More particularly, the guide catheter contains, in its structure, an elastically deformable external tube, receiving the delivery catheter, with, in the thickness of this external tube, two diametrically opposed lumens into which a cable extends freely from one end of the catheter to the other. At their proximal end, the cables are connected to a mobile part incorporated to the handle and whose displacement is controlled by the practitioner, for example by means of a button or levers at his/her disposal on the handle. The operation consists in exerting through these means a different traction on the two diametrically opposed cables so as to tighten one cable more strongly than the other: the so-exerted differential constraint has for effect to bend the elastically deformable tube, and hence the guide catheter, to the more tightened cable side. Moreover, as the deformable tube has a variable stiffness along its length, for example more flexible at its distal portion (to-be-implanted capsule side) and more rigid in its proximal region (handle side), the bend will be essentially formed in the region of the guide catheter distal end, i.e. where the tip containing the capsule to be directed has to be steered towards the target implantation site.

One of the drawbacks of this implantation material is the large overall diameter of the guide catheter, due to its thickness that must be sufficient to form therein the two diametrically opposed lumens into which will slide the steering cables. To this thickness is to be added that of the delivery catheter itself (the telescopic catheter mobile within the guide catheter, carrying the capsule to be extended and screwed) as well as that of the external protective sheath of the guide catheter. Moreover, a sufficient clearance must be provided between the guide catheter and the delivery catheter, not only to allow the free sliding and the free rotation of the delivery catheter within the guide catheter, but also to allow with a sufficient flow rate the circulation of a flushing liquid during the whole duration of the implantation operation. The flushing liquid is injected from the handle into one of the internal lumens of the delivery catheter, up to the implantation region.

In practice, for a diameter of the order of 0.4 mm for the two lumens for the passage of the cables, formed in the thickness of the guide catheter, and taking into account the sufficient clearance that must be left between the delivery catheter and the guide catheter, the typical overall diameter of the current guide catheters of this type is never lower than 18 French, i.e. 6 mm.

This leads to guide catheters of relatively large diameter, which makes them difficult to introduce and advance over the whole length of the peripheral venous network, from the femoral access site to the heart.

BRIEF SUMMARY OF THE INVENTION

One of the objects of the invention is to remedy this difficulty, by proposing a new structure for a steerable catheter having a substantially reduced overall diameter with respect to the tools currently at the disposal of the practitioners, however with similar performances, i.e. with identical or even increased possibilities of control of the bending during the implantation procedure, and of free circulation of the flushing fluid during the whole duration of the operation.

Another object of the invention is to propose such a steerable catheter structure whose fabrication cost is reduced, in particular thanks to parts in reduced number and of simple shapes, and through the use of materials, technologies and components that have been proven in similar applications.

For that purpose, the invention proposes a tool for intracorporeal implantation of a medical device, the tool having a steerable catheter including a flexible tubular unit comprising a mobile tube received within an intermediate tube.

According to the invention, the mobile tube and the intermediate tube are coaxial to each other, extend from a proximal end to a distal end of the steerable catheter and are mounted telescopically into each other with possibility of mutual rotation and mutual axial translation. The mobile tube comprises at least one central lumen located radially in a central region near an axis of the steerable catheter and extending axially from the proximal end to the distal end. The intermediate tube comprises over its whole length a longitudinal notch radially offset in a direction of offset with respect to the axis of the steerable catheter and extending axially from the proximal end to the distal end. The longitudinal notch contains a cable adapted to undergo a traction exerted from the proximal end, the traction generating a bending of the steerable catheter directed towards the offset direction, and the steerable catheter further comprises around the intermediate tube a sealed external sheath surrounding the intermediate tube over its periphery and covering the longitudinal notch over its length.

According to various subsidiary advantageous features:
the intermediate tube and the external sheath are jointly movable in rotation and translation;
a cross-sectional area of the cable is lower than a cross-sectional area of the notch, so as to leave a free space for the circulation of a flushing fluid between the proximal end and the distal end of the steerable catheter;
the mobile tube comprises a core comprising the at least one lumen, and a envelop tube surrounding the core, the envelop tube being made of a material different from a material of the core, and the core and the envelop tube being preferably jointly movable in rotation and translation;
a bending stiffness of the external sheath is a variable stiffness, decreasing from the proximal end to the distal end;
in this latter case, the external sheath preferably comprises a plurality of distinct sections following each other in the axial direction, each section having its own stiffness, and the stiffness of a given section being higher than the stiffness of the adjacent section in the distal direction and lower than the stiffness of the adjacent section in the proximal direction; preferably, each section has a substantially constant stiffness over a length of the section, except in a transition region at an interface with an adjacent section, the stiffness in the transition region showing a gradient with the stiffness of the adjacent section, typically with a length in axial direction of the transition region lower than 30 mm;
the intermediate tube is made of a substantially non-compressible material;
the overall diameter of the tubular unit is lower than or equal to 16 French (5.33 mm); and
the distal end of the mobile tube is integral with a member for coupling the mobile tube to a medical device to be implanted, and the distal end of the intermediate tube is integral with a tubular protective sleeve defining an inner volume adapted to receive the medical device to be implanted, with a degree of freedom in axial sliding and a degree of freedom in mutual rotation of the medical device to be implanted with respect to the tubular protective sleeve.
the cable, at its distal end, is axially integral with the tubular protective sleeve.

BRIEF DESCRIPTION OF THE DRAWINGS

The foregoing and other objects, aspects and advantages of the invention will be better understood from the following detailed description of a preferred embodiment of the invention with reference to the appended drawings, in which the same numerals refer to identical or functionally similar features over the different figures.

DETAILED DESCRIPTION OF A PREFERRED EMBODIMENT OF THE INVENTION

With reference to the drawings, we will now describe an exemplary embodiment of the invention.

Figure 1:
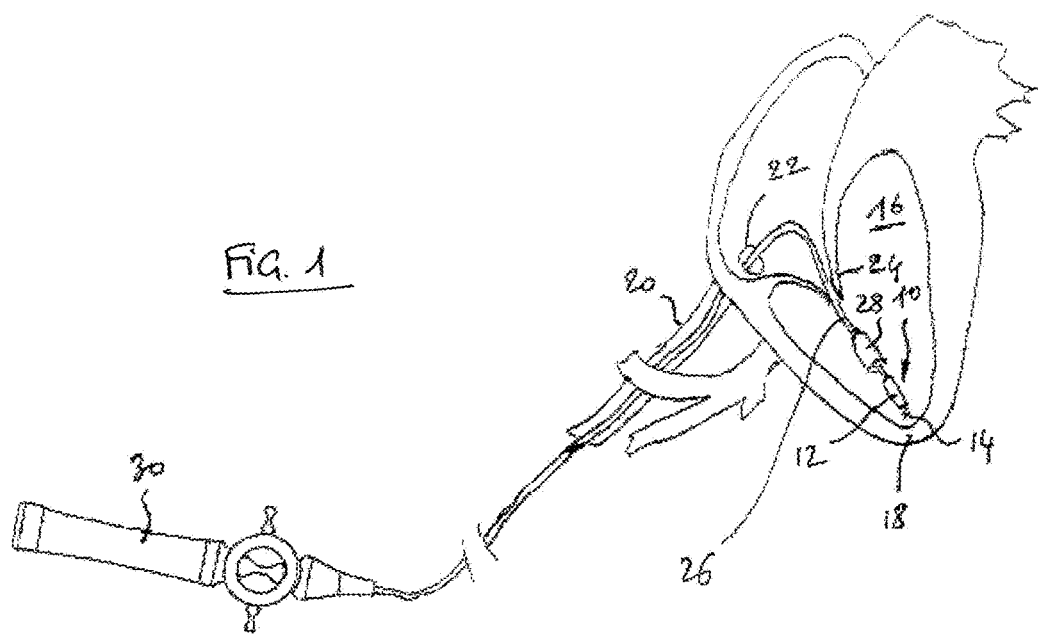
FIG. 1 is an overall view illustrating an implantation accessory coupled to a leadless capsule, in situation during an operation of implantation of this capsule into the right ventricle of the myocardium.
Figure 2:
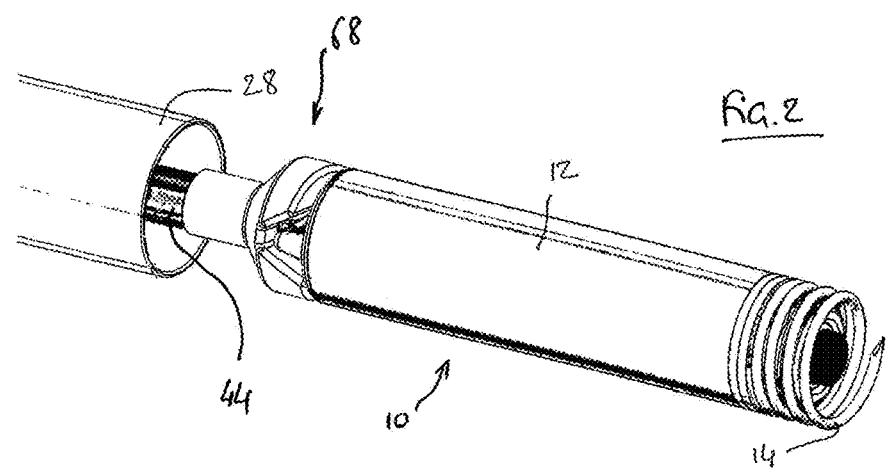
FIG. 2 illustrates a leadless capsule coupled to a catheter of the implantation accessory, extended out of a protective sleeve.
Figure 3:
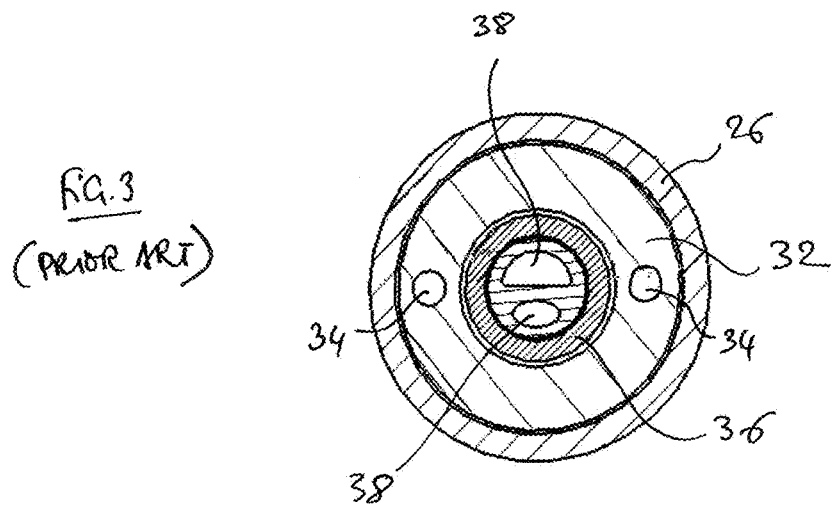
FIG. 3 is a cross-sectional view, along a radial plane, of a steerable catheter according to the prior art, showing the different elements of the internal structure of this catheter.
Figure 4:
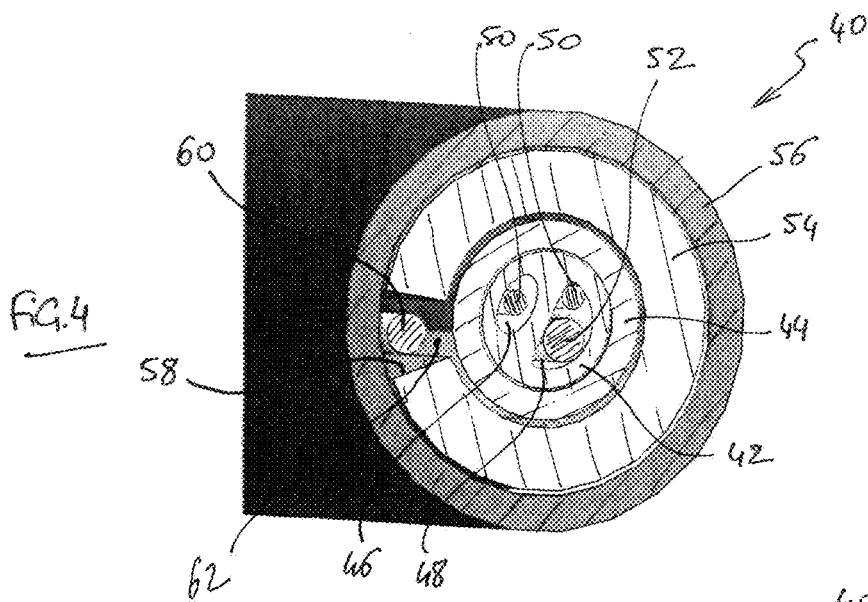
FIG. 4 is a cross-sectional view, along a radial plane, of a steerable catheter according to the invention, showing the different elements of the internal structure of this catheter.

FIGS. 1 and 2 illustrate an implantation accessory coupled to a leadless capsule, in situation during an operation of implantation of this capsule into the right ventricle of a myocardium. FIG. 1 is a general overall view, and FIG. 2 shows, in an enlarged view, the leadless capsule, extended out of the protective sleeve located at the end of the implantation catheter.

The capsule, denoted 10, comprises in a manner known per se a tubular body 12 provided at one of its ends with a protruding helical anchoring screw 14 extending axially the tubular body 12 and integral in rotation with the latter. The anchoring screw comprises, in its distal portion, a length of the order of 1.5 to 2 mm of non-contiguous turns, intended to enter the cardiac tissue so as to fasten the capsule thereto.

Here and hereinafter, the term "proximal" (or "back") will be considered with respect to the implantation tool, i.e. towards the handle operated by the practitioner; likewise, the term "distal" (or "front") will refer to an opposite direction, hence close to the implantation site and to the capsule.

In the different figures appended, these proximal and distal directions correspond respectively to the left and the right. Likewise, the term "axial" will be used with reference to the axis of the capsule, i.e. the longest dimension of the capsule, herein the axis of the cylindrical body 12, a "radial" direction being a direction located in the plane perpendicular to the axial direction.

In the example illustrated, the capsule is implanted in the right ventricle 16 of a heart, in the bottom of this ventricle in the region of the apex 18. Access to the right ventricle 16 is made through the vena cava 20, via the sinus 22, then the tricuspid valve 24, following a procedure well known per se and described for example in above-mentioned US 2014/0378991.

The implantation tool comprises for that purpose a guide catheter 26 with, at its distal end, a tubular protective sleeve 28 receiving the capsule, the latter being progressively extended out of the sleeve up to be docked to the cardiac wall. The protective sleeve 28 is intended to receive the capsule, and in particular the anchoring screw 14, during the progression in the venous network, during the passage through the valve, etc., to protect the surrounding tissues from the potential risks of tearing by the screw before the latter reaches its definitive position.

At the opposite, proximal end, the catheter is connected to an operating handle 30 operated by the practitioner.

Using various levers and buttons, the practitioner steers and makes progress the guide catheter along the vena cava 20, then accurately steers the distal end up to the docking to the bottom of the ventricle 16. Once the capsule has contacted the implantation site, the practitioner operates a translation of the capsule in the distal direction, which has for effect to extend the latter out of the tubular protective sleeve 28 (in a configuration such as that illustrated in FIG. 2). It then transmits to the capsule, via a delivery catheter received in the guide catheter 26 and operated from the handle 30, a combined movement of translation to press the distal end of the capsule against the wall, and of rotation to screw the capsule so as to anchor the later into this wall. The rotation is continued until the front face of the tubular body 12, which carries an electrode (not shown), contacts the wall. In this position, which is the final position of the capsule, the practitioner can then uncouple the delivery catheter from the capsule, then proceed to the removal of the guide catheter out of the organism by the reverse operation to that which had allowed the implantation.

The guide catheter 26 includes in its internal region a steerable catheter tube 32 integral, on the proximal side, with the handle 30 and, on the distal side, with the sleeve 28. This steerable catheter 32 comprises, in its thickness, two lumens 34 of closed contour, diametrically opposed to each other with respect to the central axis of the catheter. These lumens are intended to receive and allow the displacement of respective steering cables, remotely operated from the handle 30, which includes for that purpose a mechanism such as that described in above-mentioned U.S. Pat. No. 5,891,088 (Thompson et al.) and U.S. Pat. No. 5,462,527 (Stevens-Wright et al.), making it possible to exert on cables 34 a differential traction resulting in a bending of the distal region of the catheter.

Inside the steerable catheter 32 slides a delivery catheter 36 comprising one or several central lumens 38 intended in particular for the passage of a safety wire and for the introduction of a flushing liquid.

The safety wire is a flexible holding wire that remains, temporarily or definitively, connected to the capsule after delivery of the latter to the implantation site and uncoupling from the delivery catheter. It plays a role of "Ariadne thread" making it possible to find the capsule to again guide a catheter to it, in case of new intervention made necessary after a first non-satisfying electrical test at the initially-reached implantation site.

The flushing consists in injecting into the region of the implantation site a flushing liquid, or a contrast product making it possible to accurately follow the operation under an image intensifier.

Taking into account this structure, and in particular the necessity to receive the two steering cables in the sealed lumens 34 arranged in the thickness of the steerable catheter 32, the overall diameter of such a catheter according to the state of the art being never lower that about 18 French, i.e. 6.0 mm.

An exemplary steerable catheter made according to the teachings of the present invention will now be described, with reference to FIGS. 4 to 9. This steerable catheter 40 comprises a mobile tube acting as a delivery catheter. This mobile tube comprises a core 42 surrounded and protected by a envelop tube 44. The core 42 comprises central lumens, for example, in the illustrated example, two lumens 46, 48 serving for the passage of a safety wire 50 and possibly a cable 52 for controlling an implantation tool located on the distal side.

The safety wire 50 extends over the whole length of the catheter, with a first portion of the wire that enters through the proximal end of the lumen 46, runs through the catheter along the whole length thereof until exiting through the lumen 46 on the distal side, forms a loop (for example about a ring or similar element on the back of the capsule), then goes back through the other lumen 48 along the whole length of the catheter, in the reverse direction, up to the proximal end of the latter. The two extremities of the safety wire, which exit freely from the distal end, may be grasped at will by the practitioner, this safety wire acting as an "Ariadne thread" to be able, if needed, to find the capsule fastened at the implantation site.

When present, the cable 52 is useful to control an implantation tool located on the distal side, for example a clamp for grasping or releasing the capsule during an implantation or explantation procedure. If such a mechanism (that do not belong to the invention) is used, the cable 52 allows controlling from the handle 30, located at the proximal end of the catheter, operations of opening/closing of the clamp located at the opposite, distal end.

At its distal end 66 (visible in FIGS. 2 and 7), the mobile tube consisted of the core 42 and of the envelop tube 44 is fastened to a coupling member 68 (shown in FIG. 2) for transmitting to the capsule the required movements of axial translation and rotation, imparted from the handle 30 on the proximal side. The mobile tube may hence act as a delivery catheter.

This mobile tube 42, 44 is introduced into an intermediate tube 54 with, inside the latter, a double degree of freedom in mutual rotation and in axial translation. The intermediate tube 54 is surrounded and protected by a sealed external sheath 56.

Characteristically of the invention, a longitudinal notch 58 is formed along the length and thickness of the intermediate tube 54.

More precisely, in the radial direction, the longitudinal notch 58 extends from the external surface of the envelop tube 44 up to the internal surface of the sealed external sheath 56, hence over the thickness of the intermediate tube 54 (thickness that is, for example, of the order of 1.5 to 1.7 mm, typically of about 1.6 mm). In cross-sectional view, the longitudinal notch 58 extends over an angular sector of the order of 25 to 35°, typically about 30°.

Figure 5:
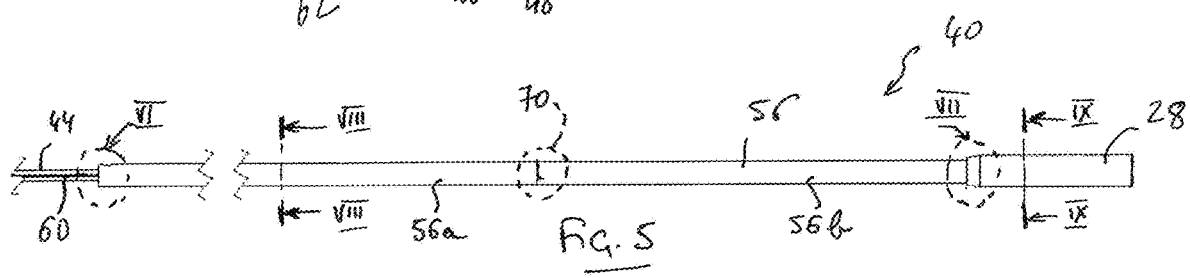
FIG. 5 is an overall top view of a catheter according to the invention, from its proximal end to its distal end.
Figure 6:
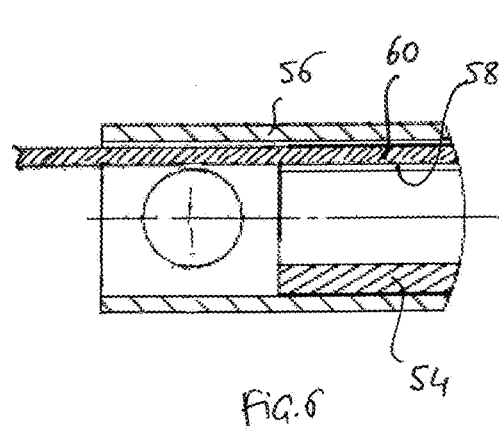
FIG. 6 is an enlarged cross-sectional view, along an axial plane, of the detail denoted VI in FIG. 5.
Figure 7:
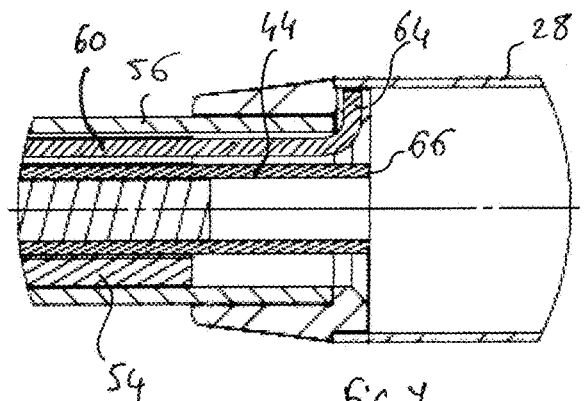
FIG. 7 is an enlarged cross-sectional view, along an axial plane, of the detail denoted VII in FIG. 5.
Figure 8:
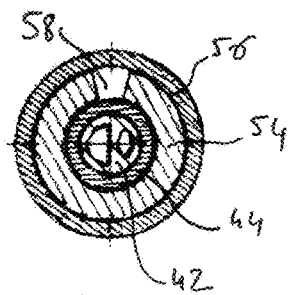
FIG. 8 is a cross-sectional view, along a radial plane VIII-VIII in FIG. 5, of the catheter according to the invention.
Figure 9:
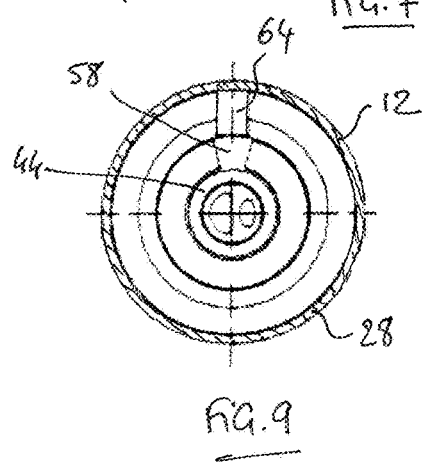
FIG. 9 is a cross-sectional view, along a radial plane IX-IX in FIG. 5, of the catheter according to the invention.

The longitudinal notch 58 defines a space 62 receiving a steering cable 60 that extends along the whole length of the catheter. On the proximal side, the steering cable 60 exits freely from the catheter (as can be seen in FIGS. 5 and 6), where it will possible to connect it to an operating tool (not shown) located in the handle 30 so as to be able to exert from the handle a controlled axial traction to the cable 60. A its opposite, distal end, the cable is on the other hand fastened to the tubular protective sleeve 28, as illustrated in 64 in FIG. 7.

The cross-section of the space 62 defined by the longitudinal notch 58 is moreover sufficient, after deducing the cross-section of the steering cable 60, to allow the free circulation of a flushing liquid injected from a flushing valve located near the handle 30, at the protruding proximal end of the catheter.

The material of the intermediate tube 54 is for example a polyamide of the nylon type 12 such as the Grilamid (registered trademark) L25. The material of the external sheath 56 is for example a thermoplastic elastomer of the PEBA (polyether block amid copolymer) type such as the Pebax (registered trademark). To facilitate the introduction into and the sliding in the venous and cardiac network, the external sheath 56 may further be provided, in a manner known per se, with a suitable external coating, for example a coating made of a low friction coefficient hydrophilic film.

Moreover, the external sheath 56 comprises a plurality of distinct sections following each other in the axial direction. In FIG. 5, two successive sections, i.e. a proximal section 56a and a distal section 56b, are illustrated, but the catheter may include a higher number of such sections.

Each section has its own stiffness, resulting from the use of a different grade of the material (for example, a PEBA) constituting the external sheath and/or a different thickness of the external sheath. These parameters are chosen in such a manner that the stiffness of a given section is higher than the stiffness of the adjacent section in the distal direction and lower than the stiffness of the adjacent section in the proximal direction.

In the simplest example illustrated in FIG. 5 of two sections 56a and 56b, the proximal section 56a has a stiffness higher than that of the section 56b, which will hence be more flexible: this increased flexibility corresponds to the region of the catheter in which it will be necessary to more strongly bend the latter, as can be seen for example in FIG. 1, where the most bent portion is the distal portion, inside the cardiac chambers. The respective lengths of the different sections are moreover chosen so as to correspond to the anatomic characteristics of the access pathway contemplated for the implantation.

Characteristically of the invention, the traction exerted to the steering cable 60 on the distal side by a suitable member of the handle 30 will have for effect to generate a bending of the intermediate tube 54 and hence of the catheter, mainly at the most flexible section, i.e. the distal section 56b in the illustrated example.

More precisely, this bending of the catheter results from the fact that, on the one hand, the cable 60 is offset with respect to the axis of the catheter and that, on the other hand, the intermediate tube 54 doesn't have a radially isotropic structure due to the presence of the notch 58.

Hence, a more or less accentuated effort exerted on the cable 60 will have for effect to tighten the latter (whose distal end is integral, in 54, with the sleeve 28) and, by reaction, to bend the catheter approximately in a plane containing the notch 58 and the cable 60 in bent configuration. The different stiffness of the successive sections of the external sheath will produce, due to the longitudinal stiffness gradient, a more accentuated bending on the distal side (section 56b) than on the proximal end. By a suitable choice of the number of sections and of their respective stiffness (technique known per se, which won't be described in more detail for this reason), it is hence possible to localize the bending ability of the catheter in the areas in which it is necessary.

It will be noted that, to obtain the desired effect, it is desirable that the stiffness gradient is abrupt enough in the region 70 of the interface between two successive sections of the envelope tube 56. The transition area 70 has for example a length in axial direction comprised between 0 and 30 mm.

Another important aspect to ensure a good steerability of the catheter by the operation of the cable 60 is the character substantially incompressible of the material of the external sheath 56. The chosen material (thermoplastic elastomer PEBA) provides this property, which may be accentuated by reinforcing the external sheath by a metallic braid, according to a technique known per se.

The typical dimensions of a structure such as that which has just been described are, by way of non-limitative example:
- mobile tube (core 42 and envelop tube 44): external diameter 2.50 mm;
- intermediate tube 54: internal diameter 2.70 mm and external diameter 4.30 mm;
- external sheath 565: external diameter 5.33 (16 French).

This small overall diameter of 16 French offers a high dimensional gain with respect to a conventional steerable catheter, whose external diameter is never lower than about 18 French.

The invention claimed is:

1. A tool for the intracorporeal implantation of a medical device, the tool having a steerable catheter including a flexible tubular unit comprising a mobile tube received inside an intermediate tube,
   wherein the mobile tube and the intermediate tube are coaxial to each other, extend from a proximal end to a distal end of the steerable catheter and are telescopically mounted into each other and configured for mutual rotation and mutual axial translation,
   wherein the mobile tube comprises at least one central lumen located radially in a central region near an axis of the steerable catheter and extending axially from the proximal end to the distal end,
   wherein the intermediate tube comprises along its whole length a longitudinal notch radially offset in a direction of offset with respect to the axis of the steerable catheter and extending axially from the proximal end to the distal end,
   wherein the longitudinal notch contains a cable adapted to undergo a traction exerted from the proximal end, the traction generating a bending of the steerable catheter directed towards the offset direction, and
   wherein the steerable catheter further comprises around the intermediate tube a sealed external sheath surrounding the intermediate tube over a periphery of the intermediate tube and covering the longitudinal notch over the length of the longitudinal notch,
   wherein a distal end of the mobile tube is integral with a member for coupling the mobile tube to a medical device to be implanted, and a distal end of the intermediate tube is integral with a tubular protective sleeve defining an inner volume adapted to receive the medical device to be implanted, with a degree of freedom in axial sliding and a degree of freedom in mutual rotation of the medical device to be implanted with respect to the tubular protective sleeve, and
   wherein a distal end of the cable is axially integral with the tubular protective sleeve.

2. The tool of claim 1, wherein the intermediate tube and the external sheath are jointly movable in rotation and translation.

3. The tool of claim 1, wherein a cross-sectional area of the cable is lower than a cross-sectional area of the notch, so as to leave a free space for the circulation of a flushing fluid between the proximal end and the distal end of the steerable catheter.

4. The tool of claim 1, wherein the mobile tube comprises a core comprising the at least one central lumen, and an envelop tube surrounding the core, the envelop tube being made of a material different from the material of the core.

5. The tool of claim 4, wherein the core and the envelop tube are jointly movable in rotation and translation.

6. The tool of claim 4, wherein a bending stiffness of the external sheath is a variable stiffness, decreasing from a proximal end to a distal end of the external sheath.

7. The tool of claim 6, wherein the external sheath comprises a plurality of distinct sections following each other in the axial direction, each section having its own stiffness, and the stiffness of a given section being higher than the stiffness of the adjacent section in the distal direction and lower than the stiffness of the adjacent section in the proximal direction.

8. The tool of claim 7, wherein each section has a substantially constant stiffness over a length of the section, except in a transition area at an interface with an adjacent section, the stiffness in the transition area showing a gradient with the stiffness of the adjacent section.

9. The tool of claim 8, wherein a length of each transition area in the axial direction is lower than 30 mm.

10. The tool of claim 1, wherein the intermediate tube is made of a substantially non-compressible material.

11. The tool of claim 1, wherein an overall diameter of the flexible tubular unit is lower than or equal to 16 French (5.33 mm).

* * * * *